US00PP14456P29

(12) United States Plant Patent
Utecht

(10) Patent No.: US PP14,456 P2
(45) Date of Patent: Jan. 13, 2004

(54) GERANIUM PLANT NAMED 'FISCASEYE'

(50) Latin Name: *Pelargonium zonale L'Hèritier*
Varietal Denomination: Fiscaseye

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,663

(22) Filed: Sep. 30, 2002

(51) Int. Cl.[7] ..... A01H 5/00
(52) U.S. Cl. ..... Plt./325
(58) Field of Search ..... Plt./325

(56) References Cited

PUBLICATIONS

GTITM UPOVROM Citation for 'Fiscaseye' as per DE PBR PEL01563; Jul. 1, 1999.*
Blatt Für Sortenwesen, Official Gazette of the German Bundessortenamtes for Plant Breeder's Rights; pp.: cover, 264; Aug. 15, 1999 (German PBR application publication).
Blatt Für Sortenwesen, Official Gazette of the German Bundessortenamtes for Plant Breeder's Rights; pp.: cover, 305, 307; Sep. 15, 2000 (German PBR proposal for final denomination publication).
Blatt Für Sortenwesen, Official Gazette of the German Bundessortenamtes for Plant Breeder's Rights; pp.: cover, 400; 401 Dec. 15, 2000 (German PBR grant publication).
Bulletin des Variétés Végétales / Plant Varieties Journal, No. 42, Canadian Plant Breeders' Rights Office, pp.: cover, 15; Jan. 2002 (proposed denomination publication).
Bulletin des Variétés Végétales / Plant Varieties Journal, No. 42, Canadian Plant Breeders' Rights Office, pp.: cover, 109–110; Jan. 2003 (application under examination publication).
Bundesamt für Landwirtschaft, Swiss Patent, Design and Trademark Gazette No. 152, Jul. 31, 2002.
Official Gazette of the Community Plant Variety Office, European Community, Aug. 15, 2002 (application; proposed denomination publication).
Official Gazette of the Community Plant Variety Office, European Community, Feb. 15, 2003 (Grant publication).

* cited by examiner

*Primary Examiner*—Kent Bell
(74) *Attorney, Agent, or Firm*—Foley & Lardner

(57) ABSTRACT

A new and distinct geranium plant named 'Fiscaseye' characterized by the combined features of pink semi-double flowers with rose-red eyes, floriferous with medium sized umbels, grass-green foliage with weak zonation, medium growth habit, moderately compact, low, well-branched plant habit, and medium (mid season) spring flowering response.

1 Drawing Sheet

Latin name of the genus and species of the plant claimed: *Pelargonium zonale* L'Héritier.
Variety denomination: 'Fiscaseye'.

BACKGROUND OF THE INVENTION

The present invention comprises a new and distinct cultivar of geranium, botanically known as *Pelargonium zonale,* and hereinafter referred to by the cultivar name 'Fiscaseye'.

'Fiscaseye' is a product of a planned breeding program which had the objective of creating new zonal geranium cultivars with light pink flower color, semi-double flower type, intense green foliage and medium sized, well-branched plant habit.

'Fiscaseye' originated from a hybridization made by the inventor Angelika Utecht in a controlled breeding program in Galdar, Gran Canaria, Spain, in 1997. The female parent was the unpatented commercial variety 'Goesta', characterized by semi-double, light pink flowers, the upper petals with white bases, foliage with almost no zonation, and relatively compact plant habit.

The male parent of 'Fiscaseye' was the unpatented commercial variety known as 'Dresdner Puppe Rosa mit Auge' (Plant Breeder's Rights protection in Europe under 'Drepenosa') having pink single-type flowers with deep pink macules, early flowering, medium to light green foliage with very weak zonation, and compact plant habit.

'Fiscaseye' was selected as one flowering plant within the progeny of the stated cross by Angelika Utecht in 1998 in a controlled environment in Galdar, Gran Canaria, Spain.

The first act of asexual reproduction of 'Fiscaseye' was accomplished when vegetative cuttings were taken from the initial selection in the fall of 1998 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fiscaseye' are firmly fixed and are retained through successive generations of asexual reproduction.

'Fiscaseye' has not been observed under all possible environmental conditions. The phenotype may vary significantly with variation in environment such as temperature, light intensity and day length.

The following observations, measurements, and comparisons describe plants grown in Hillscheid, Germany under greenhouse conditions which approximate those generally used in commercial practice.

BRIEF SUMMARY OF THE INVENTION

The following traits have been repeatedly observed and are determined to be basic characteristics of 'Fiscaseye' in combination distinguish this geranium as a new and distinct cultivar:

1. Round, pink colored flowers with rose-red eyes;
2. large flowers and large inflorescences;
3. grass-green foliage, relatively large leaves with slight zonation;
4. medium vigorous growth, low, rounded plant habit; and
5. medium (mid season) spring flowering response.

Of the many commercial cultivars known to the present inventor, the most similar in comparison to 'Fiscaseye', are the parental varieties 'Goesta' and 'Dresdner Puppe Rosa mit Auge', and the patented variety 'Designer Light Pink' (U.S. Plant Pat. No. 8,552), and the variety 'Fip 336' (U.S. Plant Pat. No. 14,082).

In comparison to 'Goesta', 'Fiscaseye' has a deeper and more bluish pink flower color, and petals have rose-red eyes, which lack with 'Goesta'. Furthermore, 'Fiscaseye' has larger leaves with slightly stronger zonation, and it grows more vigorously than 'Goesta'.

In contrast to 'Dresdner Puppe Rosa mit Auge', with single-type flowers, 'Fiscaseye' has weakly semi-double flower type and somewhat more intense green foliage with slightly more distinct zonation. In addition, beginning of flowering is earlier for 'Dresdner Puppe Rosa mit Auge' than for 'Fiscaseye'.

In comparison to 'Designer Light Pink', 'Fiscaseye' has larger flowers with rose-red eyes on petals, which lack with 'Designer Light Pink'. Furthermore, plant habit of 'Fiscaseye' is much more compact, and foliage has less distinct zonation.

In comparison to 'Fip 336', 'Fiscaseye' has a somewhat deeper and more uniform main flower color, shorter peduncles, and somewhat smaller, especially lower, plant habit.

BRIEF DESCRIPTION OF THE DRAWING

The accompanying photographic drawing shows typical flower and foliage characteristics of 'Fiscaseye' with colors being as true as possible with an illustration of this type. The drawing depicts a side-view of a typical flowering potted plant of 'Fiscaseye'.

DETAILED BOTANICAL DESCRIPTION

Measurements were taken in Hillscheid, Germany, in mid May 2002, about 12 weeks after planting of rooted cuttings. The plants were growing in 14 cm plastic pots and had not been pinched.

In the following description color references are made to The Royal Horticultural Society Colour Chart. The color values were determined indoors from plants developed in a green-house in May 2002 in Hillscheid, Germany.

Inflorescence:

*Type.*—Umbel, semi-spherically shaped.
*Average diameter.*—108 mm.
*Average depth.*—65 mm.
*Peduncle length.*—180 mm.
*Peduncle color.*—Light green, RHS 143 C,.
*Pedicel length.*—22 mm.
*Pedicel color.*—Light green, RHS 143 C, may in parts appear weakly infused with brown, RHS 174 B.
*Number of flowers per umbel.*—About 25–30.

Corolla:

*Average diameter.*—55 mm.
*Form.*—Semi-double.
*Shape.*—Round outline, flat cup-shape.
*Number of petaloids.*—0–2.
*Shape of petaloids.*—Tube-shaped; acute apex, acute base, margin is entire (occasionally with a single notch, and/or a deformed anther at the upper end).
*Size of petaloids.*—Variable width, 1–5 mm; variable length, 5–10 mm.
*Color of petaloids.*—68 B (inner surface); RHS N66 C, and RHS 65 B to RHS 155 D at the base (outer surface).
*Number of petals.*—5–7.
*Shape of petals.*—Obovate, base acute, apex rounded, margin is entire.
*Size of petals.*—Upper petals: 28–30 mm long, 25–28 mm wide. Lower petals: 24–26 mm long, 24–26 mm wide.
*Color (general tonality from a distance of three meters).*—Pink with rose-red eyes.
*Color of upper petals.*—Main part between RHS 68 A and 68 B; white bases, RHS 155 D.
*Markings of upper petals.*—Fine purple-pink veins, RHS 66 B, and deep pink macules, RHS 66 C.
*Color of lower petals.*—Pink, between RHS 65 A and 68 B, with lighter base: RHS 65 D.
*Markings of lower petals.*—Purple-pink to rose-red eyes, between RHS 66 B and 66 C.
*Color of lower surface of petals.*—RHS 65 A near margin, mainly RHS 65 D.
*Color of sepals.*—Outer surface: light green, RHS 144 A. Inner surface: light green, RHS 144 B.
*Number of sepals.*—5.
*Shape of sepals.*—Linear to lanceolate, acute to acuminate tip, truncate base, surface with very weak pubescence, margin entire.
*Size of sepals.*—11–13 mm long, 4 mm wide for the largest upper sepal, 2–3 mm in width for the other sepals.

Bud: (just prior to petals unfoldings):

*Shape.*—Elliptical.
*Color of sepals.*—Light green, RHS 144 A.
*Color of petals.*—Deep pink, approximately RHS 66 D.
*Length.*—18 mm.
*Width.*—9 mm.

Reproductive organs:

*Androecium.*—5–7 fertile anthers, moderate pollen, yellow-orange, RHS 30 A, filaments white, RHS 155 D.
*Gynoecium.*—One pistil, style and stigma pink, RHS 58 C, stigma 5–6-lobed.
*Fertility/seed set.*—Occasionally seed set, mainly in late summer to fall.
*Fruit.*—Oblong, about 5–6 mm wide, rostrum (beak) 38–40 mm long.
*Seed.*—Oblong, 4–5 mm long, brown, RHS 177 B.

Spring flowering response period: In Hillscheid, Germany, in 2002 plants had on average 0.5 flowers opened 8 weeks after planting of rooted cuttings.

Outdoor flower production: Continuously and rich flowering, the flower count in 2002 in Hillscheid, Germany, indicated about 4–5 inflorescence per plant in mid May.

Durability: Good stability of flower color, good rain resistance.

Lastingness of the individual flower: About 7 days at 18° C., about 16–18 days for the umbel.

Fragrance: None.

PLANT

Foliage:

*Shape.*—Kidney-shaped, rounded with weak lobes, cordate base with open gap between the lowest lobes.

*Margin.*—Bicrenate, distinctly wavy.

*Texture.*—Upper surface velvety, may appear slightly glossy.

*Size of leaf.*—Approximately 110 mm wide, 70 mm long.

*Color of upper surface.*—Medium green, approximately RHS 137 C.

*Color of zonation.*—Brown, about RHS 166 A, usually weak.

*Color of lower surface.*—RHS 137 D.

*Petioles.*—60–75 mm long (somewhat variable), 3–4 mm diameter, light green in color, approximately RHS 143 C.

General appearance and form:

*Stem.*—Green to light green in color, RHS 143 B; 12–15 cm in length.

*Internode length.*—10–15 mm.

*Branching pattern.*—6.2 branches.

*Plant size.*—Height 14 cm, width 30 cm (10 week-old plants, as described, measured from the top of the soil (base of the main stem) to the surface of the foliage canopy, without inflorescences).

*Pest/disease resistance/susceptibility.*—No observations to date.

I claim:

1. A new and distinct cultivar of geranium plant named 'Fiscaseye', as described and illustrated herein.

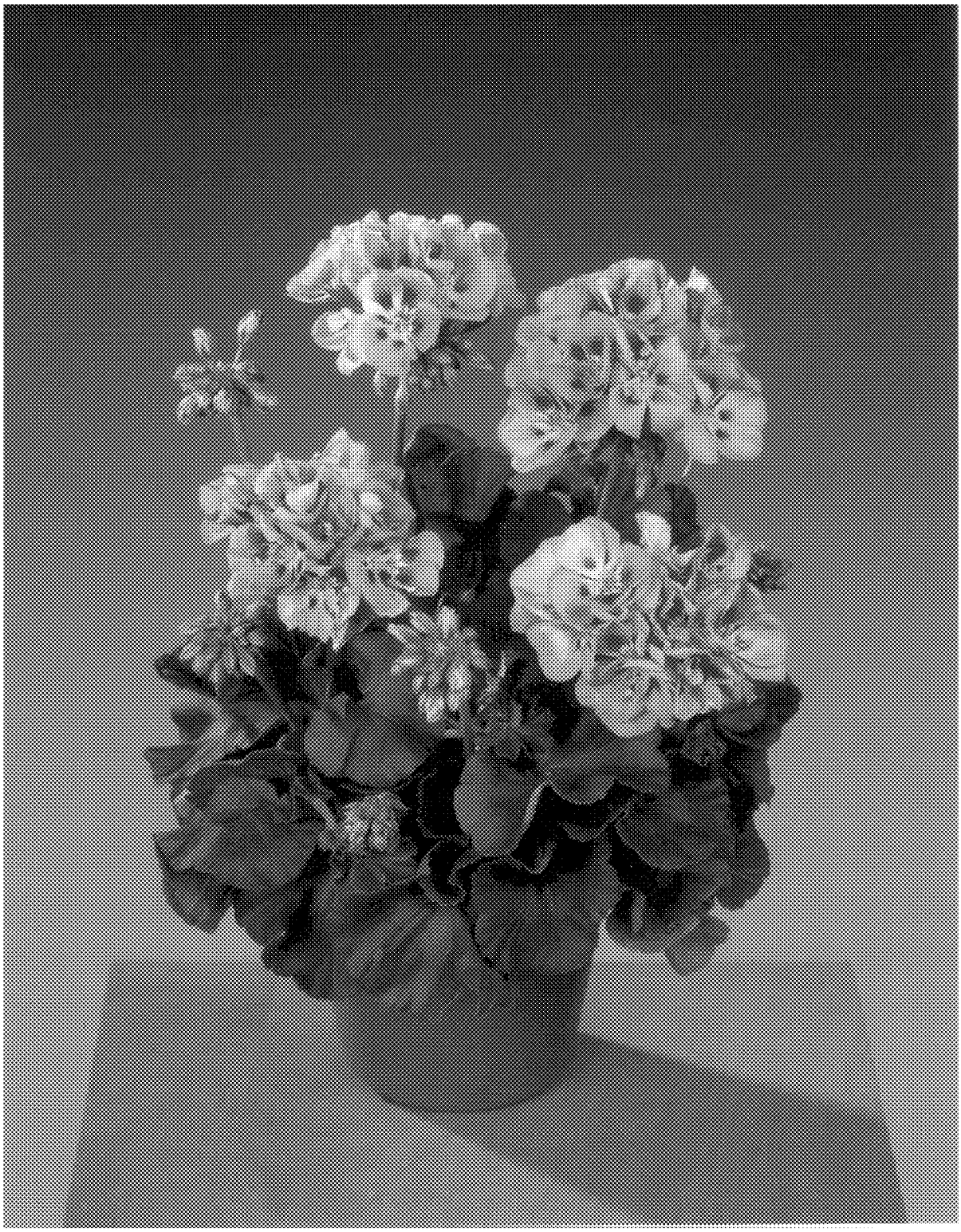

* * * * *